(12) United States Patent
Khan et al.

(10) Patent No.: US 11,539,667 B2
(45) Date of Patent: Dec. 27, 2022

(54) VIRTUAL PRIVATE NETWORK CONNECTION METHOD AND MEMORY CARD DEVICE USING SAME

(71) Applicant: Key ASIC Inc., Hsinchu County (TW)

(72) Inventors: Bahadur Shah Khan, Petaling Jaya (MY); Sek Yen Tan, Puchong (MY); Hao-Jen Wu, Hsinchu County (TW)

(73) Assignee: KEY ASIC INC., Hsinchu County (TW)

( * ) Notice: Subject to any disclaimer, the term of this patent is extended or adjusted under 35 U.S.C. 154(b) by 224 days.

(21) Appl. No.: 16/986,247

(22) Filed: Aug. 5, 2020

(65) Prior Publication Data

US 2021/0392113 A1 Dec. 16, 2021

(30) Foreign Application Priority Data

Jun. 12, 2020 (TW) .................. 109119922

(51) Int. Cl.
*H04L 29/06* (2006.01)
*H04L 9/40* (2022.01)
(Continued)

(52) U.S. Cl.
CPC .......... *H04L 63/0272* (2013.01); *G06F 9/445* (2013.01); *G06F 21/6245* (2013.01);
(Continued)

(58) Field of Classification Search
CPC ............. H04L 63/0272; H04L 12/4641; H04L 9/3263; G16H 40/67; G16F 9/445
(Continued)

(56) References Cited

U.S. PATENT DOCUMENTS 9,015,824 B1 * 4/2015 Drewry ..................... H04L 9/32
726/6
10,810,157 B1 * 10/2020 Paterra .................... G06F 3/067
(Continued)

FOREIGN PATENT DOCUMENTS

TW 201445353 12/2014
TW 201902183 1/2019
(Continued)

OTHER PUBLICATIONS

Search report from TIPO dated Jun. 30, 2021.

*Primary Examiner* — Evans Desrosiers
(74) *Attorney, Agent, or Firm* — WPAT, PC (57) ABSTRACT

A virtual private network connection method and a memory card device using the virtual private network connection method are provided. Firstly, a virtual private network connection application program is provided. Then, the virtual private network connection application program is loaded in a memory card device. Then, the memory card device is installed in a medical device. After the virtual private network connection application program is executed and the memory card device is connected to a virtual private network server according to a connection request, the data from the medical device is transmitted to the virtual private network server through the memory card device. In such way, the data will not be attacked by malware and stolen by a third-party manufacturer during the transmission process.

17 Claims, 3 Drawing Sheets

(51) Int. Cl.
*G16H 40/67* (2018.01)
*G06F 9/445* (2018.01)
*G06F 21/62* (2013.01)
*H04L 9/32* (2006.01)
*H04L 12/46* (2006.01)

(52) U.S. Cl.
CPC ........... *G16H 40/67* (2018.01); *H04L 9/3263* (2013.01); *H04L 12/4641* (2013.01)

(58) Field of Classification Search
USPC .......................................................... 726/15
See application file for complete search history.

(56) References Cited

U.S. PATENT DOCUMENTS

| | | |
|---|---|---|
| 2012/0023325 A1 | 1/2012 | Lai |
| 2019/0288860 A1* | 9/2019 | Poltorak ............. H04W 12/033 |
| 2020/0128000 A1 | 4/2020 | Pawar et al. |

FOREIGN PATENT DOCUMENTS

| | | |
|---|---|---|
| WO | WO2006021865 A1 | 3/2006 |
| WO | WO2008033554 A2 | 3/2008 |

* cited by examiner

VIRTUAL PRIVATE NETWORK CONNECTION METHOD AND MEMORY CARD DEVICE USING SAME

FIELD OF THE INVENTION

The present invention relates to a virtual private network connection method, and more particularly to a virtual private network connection method for a memory card device and a memory card device using the method.

BACKGROUND OF THE INVENTION

Nowadays, with the rapid development of electronic technology, the popularity of various electronic products is becoming higher and higher. For example, the electronic products include mobile phones, digital cameras, notebook computers, tablet computers or medical devices. As the use functions of electronic products continue to increase and expand, the amount of data to be stored in the electronic products increases gradually. In addition to the built-in memory in the electronic products, various electronic products use external memory card devices to expand the storage capacity and store more data, electronic files or application programs. The electronic files stored in the memory card device can be modified or deleted at the proper time. Moreover, new data, messages or application programs may can be stored into the memory card device.

In case that the electronic product and the memory card device with a wireless transmission function are combined together, the data stored in the memory card device can be transmitted from the electronic product to an external device or a cloud network storage space in real time in a wireless transmission manner (e.g., a WiFi transmission manner). Take the medical device having the wireless transmission memory card device for example. During the operation of the medical device, the medical data about the user's body status is generated. While the medical data is stored into the wireless transmission memory card device, the medical data is also transmitted to other electronic devices (e.g., the mobile phones of relatives or friends) or transmitted to the cloud network storage space for storage.

However, while the data is transmitted from the electronic product to other electronic devices or the cloud network storage space through the wireless transmission memory card device, the data is readily attacked by malware and or stolen by a third-party manufacturer.

Therefore, it is important to provide a safe data transmission method to overcome the drawbacks of the conventional technologies.

SUMMARY OF THE INVENTION

For overcoming the drawbacks of the conventional technology, the present invention provides a virtual private network connection method for a medical device. The medical device logins in a virtual private network server through a memory card device with a virtual private network connection application program. Consequently, during the operation of the medical device, the generated data is transmitted to the virtual private network server through the memory card device so as to be encrypted and protected.

For overcoming the drawbacks of the conventional technology, the present invention provides a memory card device. When a virtual private network connection and control module executes a virtual private network connection application program, the virtual private network connection and control module is connected to a virtual private network server. Consequently, the data stored in a storage module is transmitted to the virtual private network server through the virtual private network connection and control module so as to be encrypted and protected.

The other objects and advantages of the present invention will be understood from the disclosed technical features.

In accordance with an aspect of the present invention, a virtual private network connection method for a memory card device is provided. The virtual private network connection method includes the following steps. Firstly, a virtual private network connection application program is provided. Then, the virtual private network connection application program is loaded into the memory card device. Then, the memory card device is installed in a medical device. Then, the virtual private network connection application program is executed, and the memory card device is connected to a virtual private network server according to a connection request. Then, a data from the medical device is transmitted to the virtual private network server through the memory card device.

In an embodiment, the virtual private network connection method further includes a step of making a server connection setting before the virtual private network connection application program is executed.

In an embodiment, the server connection setting includes a certificate setting and a client parameter setting.

In an embodiment, a root CA certificate, a client certificate and a client key are generated according to the certificate setting.

In an embodiment, the client parameter setting includes a server address setting, a communication protocol setting, a device mode setting, a user name and password setting, an encryption method setting and a file compression setting.

In an embodiment, the virtual private network connection method further includes a step of judging whether a file size of the virtual private network connection application program is smaller than or equal to a storage capacity threshold value of the memory card device before the virtual private network connection application program is loaded into the memory card device. If the file size of the virtual private network connection application program is smaller than or equal to the storage capacity threshold value of the memory card device, the virtual private network connection application program is loaded into the memory card device.

In an embodiment, the storage capacity threshold value is one fourth of a total storage capacity of the memory card device.

In an embodiment, the medical device is an ultrasonic scanner, a ventilator, a fundus camera, a continuous positive airway pressure machine or a LED spectrum analyzer.

In accordance with another aspect of the present invention, a memory card device is provided. The memory card device includes an I/O interface module, a storage module and a virtual private network connection and control module. The I/O interface module is electrically connected with a medical device. A data generated by the medical device and a virtual private network connection application program are stored in the storage module. The virtual private network connection and control module is electrically connected with the I/O interface module and the storage module. When the virtual private network connection and control module executes the virtual private network connection application program and receives a connection request, the virtual private network connection and control module is connected to a virtual private network server, and the data stored in the storage module is transmitted to the virtual private network server through the virtual private network connection and control module.

In an embodiment, the virtual private network connection and control module includes a processing control unit and a virtual private network connection unit. The processing control unit is electrically connected with the I/O interface module and the storage module. The virtual private network connection unit is electrically connected with the processing control unit. When the processing control unit executes the virtual private network connection application program and receives the connection request, the virtual private network connection unit is connected to the virtual private network server under control of the processing control unit. Consequently, the data is transmitted from the virtual private network connection unit to the virtual private network server.

In an embodiment, an operation system is further stored in the storage module, and the processing control unit executes at least one of the operation system and the virtual private network connection application program.

Preferably, when the I/O interface module is electrically connected with the medical device, the processing control unit controls the I/O interface module to acquire the data from the medical device and stores the data into the storage module.

In an embodiment, the virtual private network connection unit includes a communication unit, and the communication unit is electrically connected with the processing control unit. When the processing control unit executes the virtual private network connection application program and receives the connection request, the communication unit is connected to a communication network under control of the processing control unit, so that the virtual private network connection unit is connected to the virtual private network server through the communication network.

In an embodiment, the communication unit is connected to the communication network in a wireless transmission manner or a wired transmission manner.

In an embodiment, the storage module includes a volatile memory unit and a non-volatile memory unit, and the data and the virtual private network connection application program are stored in the non-volatile memory unit.

In an embodiment, a file size of the virtual private network connection application program is smaller than or equal to one fourth of a total storage capacity of the non-volatile memory unit.

In an embodiment, the virtual private network connection application program contains a server connection setting information, and the server connection setting information contains a certificate setting information and a client parameter setting information.

In an embodiment, the certificate setting information includes a root CA certificate, a client certificate and a client key.

In an embodiment, the client parameter setting information contains an internet protocol address information, a communication protocol setting information, a device mode setting information, a user name and password setting information, an encryption method setting information and a file compression setting information.

In an embodiment, the medical device is an ultrasonic scanner, a ventilator, a fundus camera, a continuous positive airway pressure machine or a LED spectrum analyzer.

From the above descriptions, the present invention provides a virtual private network connection method and a memory card device. A virtual private network connection application program is loaded in a memory card device. The memory card device with the virtual private network connection application program is installed in a medical device. The medical device logins in a virtual private network server through the memory card device with the virtual private network connection application program. Consequently, during the operation of the medical device, the generated data is transmitted to the virtual private network server through the memory card device so as to encrypted and protected. In such way, the data will not be attacked by malware and stolen by a third-party manufacturer during the transmission process.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. In this regard, directional terminology, such as "top," "bottom," "front," "back," etc., is used with reference to the orientation of the Figure(s) being described. The components of the present invention may be located in a number of different orientations. As such, the directional terminology is used for purposes of illustration and is in no way limiting.

Figure 1:
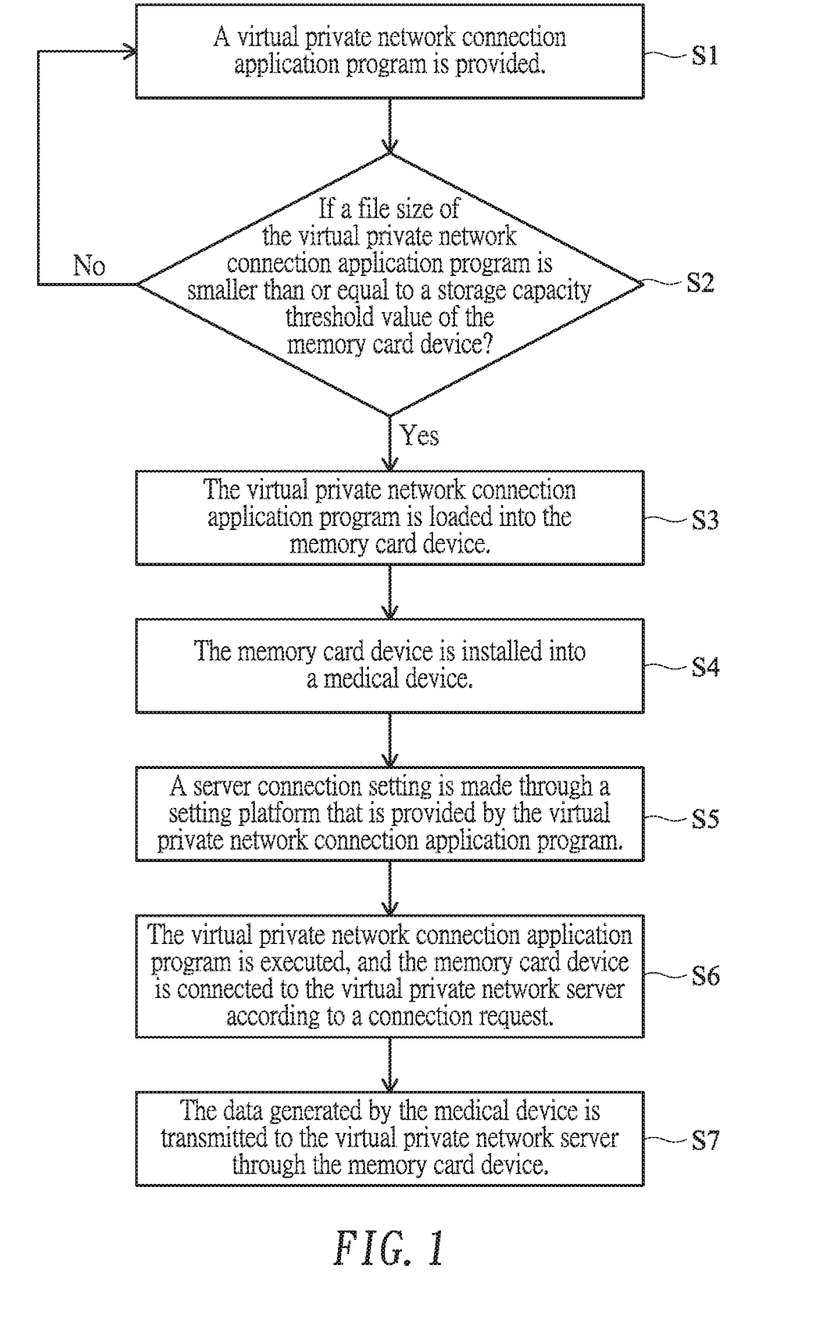
FIG. 1 is a flowchart illustrating a virtual private network connection method according to an embodiment of the present invention.

FIG. 1 is a flowchart illustrating a virtual private network connection method according to an embodiment of the present invention. The virtual private network connection method is applied to a memory card device. For example, a memory card device with a virtual private network connection application program is installed in a medical device to execute the virtual private network connection method. The medical device logins in a safe and protective virtual private network server through the memory card device. Consequently, during the operation of the medical device, the generated data (e.g., the medical data about the user's body status) can be encrypted and protected. In such way, the data will not be attacked by malware and or stolen by a third-party manufacturer during the transmission or reception process.

As shown in FIG. 1, the virtual private network connection method comprises the following steps.

In a step S1, a virtual private network connection application program is provided. That is, the user may previously download at least one of plural virtual private network connection application programs from different developers. For example, the virtual private network connection application program is an application program developed by Open VPN. It is noted that the example of the virtual private network connection application program is not restricted.

Before the virtual private network connection application program is loaded into the memory card device, a step S2 is performed to judge whether a file size of the virtual private network connection application program is smaller than or equal to a storage capacity threshold value of the memory card device. If the file size of the virtual private network connection application program is larger than the storage capacity threshold value of the memory card device, the virtual private network connection application program is not loaded into the memory card device. Then, the user may re-select another private network connection application program with the proper file size. If the file size of the virtual private network connection application program is smaller than or equal to a storage capacity threshold value of the memory card device, the virtual private network connection application program is loaded into the memory card device (Step S3).

In an embodiment, the storage capacity threshold value of the memory card device is one fourth of the total storage capacity of the memory card device. It is noted that the storage capacity threshold value of the memory card device is not restricted. That is, the storage capacity threshold value may be increased or decreased according to the practical requirements. Especially, the memory card device comprises a non-volatile memory unit and a volatile memory unit. The total storage capacity of the memory card device indicates the total storage capacity of the non-volatile memory unit. In an embodiment, the memory card device is a secure digital memory card (also abbreviated as SD card or a Micro SD card.

Then, the memory card device with the virtual private network connection application program is installed into a medical device (Step S4). An example of the medical device includes but is not limited to an ultrasonic scanner, a ventilator, a fundus camera, a continuous positive airway pressure (CPAP) machine or a LED spectrum analyzer.

Then, a server connection setting is made through a setting platform that is provided by the virtual private network connection application program (Step S5). The server connection setting includes a certificate setting and a client parameter setting. In the process of making the certificate setting, a root CA certificate is generated, a client certificate is generated, and a client key is generated. The two-way authentication between the server and the client is performed through the above certificates. In an embodiment, the client parameter setting includes a server address setting, a communication protocol setting, a device mode setting, a user name and password setting, an encryption method setting and a file compression setting. Especially, the server address setting is used to provide an internet protocol address (IP address) for the client to use. The communication protocol setting allows for the selection of a user data packet protocol (UDP) or a transmission control protocol (TCP). The device mode setting allows for the selection of a TUN mode or a TAP mode. According to the user name and password setting, the user can login in the virtual private network server through the set user name and the set password so as to acquire the data from the virtual private network server. The encryption method setting allows for the selection of a Blow Fish encryption method, an AES-128 encryption method, an AES-256 encryption method, a Triple-DES encryption method or a cipher BF-CBC encryption method. The file compression setting allows for the selection of enabling the file compression function or disabling the file compression function.

In a step S6, the virtual private network connection application program is executed, and the memory card device is connected to the virtual private network server according to a connection request. In an embodiment, after the virtual private network connection application program is executed and the connection request is received, the memory card device is connected to a communication network and then the memory card device is connected to the virtual private network server through the communication network. In an embodiment, an operation system is loaded in the memory card device. When the operation system is executed, the virtual private network connection application program can be operated under a graphic-based operation interface that is provided by the operation system.

In a step S7, the data generated by the medical device is transmitted to the virtual private network server through the memory card device so as to be encrypted and protected. In case that the medical device is a ventilator, the generated data of the medical device is the real-time data about the user's respiratory status during the operation of the ventilator. For example, the real-time data includes flow, resistance, pressure and any other appropriate operating data. That is, the real-time data include the so-called respiratory parameters. The respiratory parameters contain the oxyhemoglobin saturation by pulse oximetry (SPO2) of the user, the current spontaneous tidal volume value of the user and the current spontaneous breath number of the user. The contents of the respiratory parameters may be determined according to the practical requirements. For example, preferably but not exclusively, the respiratory parameters further contain the positive end expiratory pressure (PEEP), the airway resistance (Rexp), the expiratory flow (Fexp) and the expiratory flow waveform information.

Hereinafter, the architecture of the memory card device with the virtual private network connection application program will be described in more details as follows.

Figure 2:
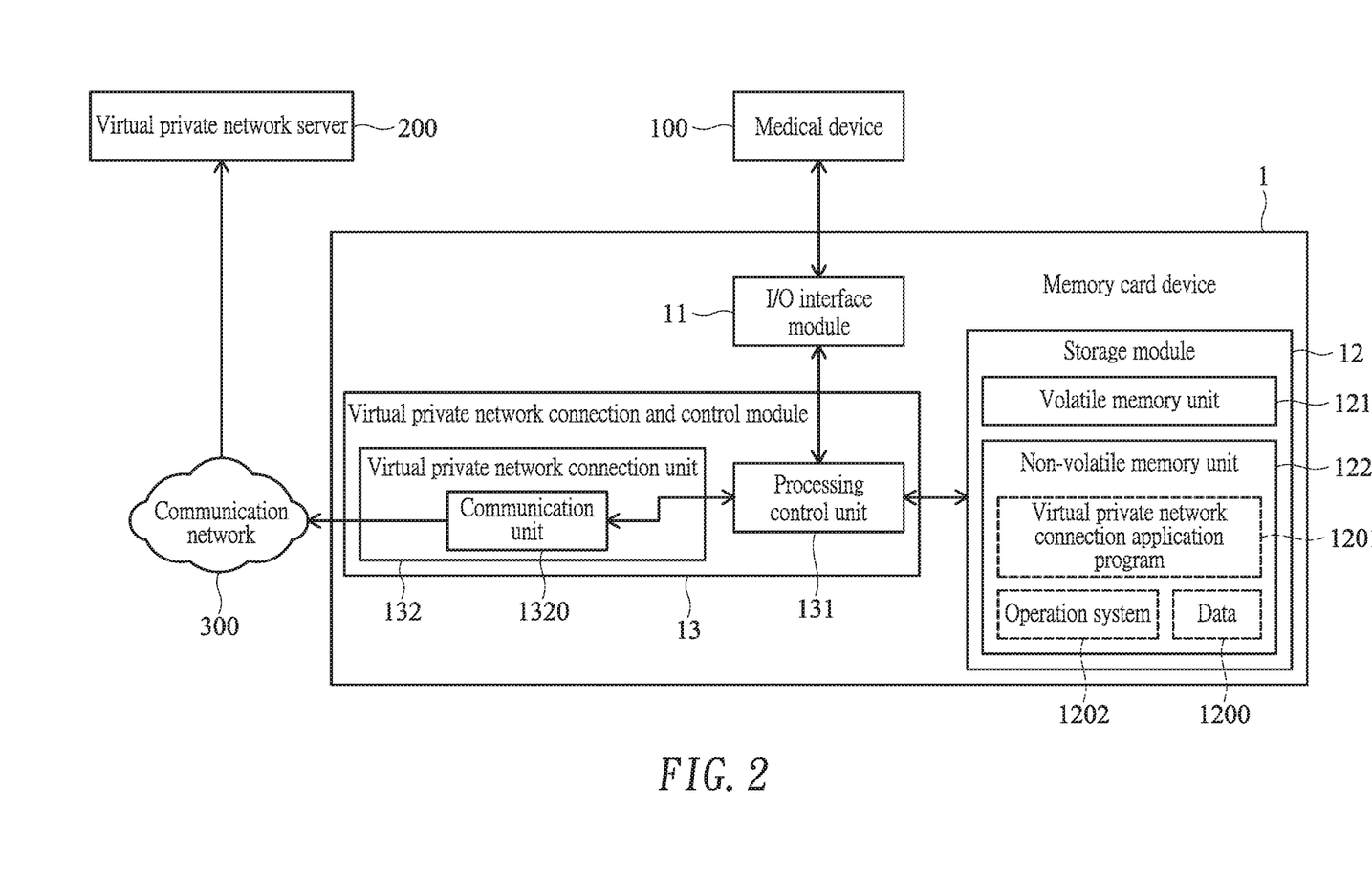
FIG. 2 is a schematic functional block diagram illustrating a memory card device according to an embodiment of the present invention.

FIG. 2 is a schematic functional block diagram illustrating a memory card device according to an embodiment of the present invention. As shown in FIG. 2, the memory card device 1 comprises an I/O interface module 11, a storage module 12 and a virtual private network connection and control module 13. The I/O interface module 11 is electrically connected with a medical device 100. The data 1200 generated by the medical device 100 is stored in the storage module 12. In addition, a virtual private network connection application program 1201 is stored in the storage module 12. The virtual private network connection and control module 13 is electrically connected with the I/O interface module 11 and the storage module 12.

When the virtual private network connection and control module 13 executes the virtual private network connection application program 1201 and receives a connection request, the virtual private network connection and control module 13 is connected to a virtual private network server 200. Consequently, the data 1200 stored in the storage module 12 is transmitted to the virtual private network server 200 through the virtual private network connection and control module 13.

For example, the medical device 100 is an ultrasonic scanner, a ventilator, a fundus camera, a continuous positive airway pressure (CPAP) machine or a LED spectrum analyzer. It is noted that the type of the medical device 100 is not restricted.

As shown in FIG. 2, the virtual private network connection and control module 13 comprises a processing control unit 131 and a virtual private network connection unit 132. The processing control unit 131 is electrically connected with the I/O interface module 11 and the storage module 12. The virtual private network connection unit 132 is electrically connected with the processing control unit 131. When the processing control unit 131 executes the virtual private network connection application program 1201 and receives the connection request, the virtual private network connection unit 132 is connected to the virtual private network server 200 under control of the processing control unit 131. Consequently, the data 1200 can be transmitted to the virtual private network server 200 through the virtual private network connection unit 132.

When the virtual private network connection and control module 13 executes the virtual private network connection application program 1201 and receives a connection request, the virtual private network connection and control module 13 is connected to a virtual private network server 200. Consequently, the data 1200 stored in the storage module 12 is transmitted to the virtual private network server 200 through the virtual private network connection and control module 13.

For example, the medical device 100 is an ultrasonic scanner, a ventilator, a fundus camera, a continuous positive airway pressure (CPAP) machine or a LED spectrum analyzer. It is noted that the type of the medical device 100 is not restricted.

As shown in FIG. 2, the virtual private network connection and control module 13 comprises a processing control unit 131 and a virtual private network connection unit 132. The processing control unit 131 is electrically connected with the I/O interface module 11 and the storage module 12. The virtual private network connection unit 132 is electrically connected with the processing control unit 131. When the processing control unit 131 executes the virtual private network connection application program 1201 and receives the connection request, the virtual private network connection unit 132 is connected to the virtual private network server 200 under control of the processing control unit 131. Consequently, the data 1200 can be transmitted to the virtual private network server 200 through the virtual private network connection unit 132.

When the I/O interface module 11 is electrically connected with the medical device 100, the processing control unit 131 controls the I/O interface module 11 to acquire the data 1200 from the medical device 100 and stores the data 1200 into the storage module 12. For example, in case that the medical device is a ventilator, the generated data 1200 is the real-time data about the user's respiratory status during the operation of the ventilator. For example, the real-time data includes flow, resistance, pressure and any other appropriate operating data. That is, the real-time data include the so-called respiratory parameters. The respiratory parameters contain the oxyhemoglobin saturation by pulse oximetry (SPO2) of the user, the current spontaneous tidal volume value of the user and the current spontaneous breath number of the user. The contents of the respiratory parameters may be determined according to the practical requirements. For example, preferably but not exclusively, the respiratory parameters further contain the positive end expiratory pressure (PEEP), the airway resistance (Rexp), the expiratory flow (Fexp) and the expiratory flow waveform information.

As shown in FIG. 2, the storage module 12 comprises a volatile memory unit 121 and a non-volatile memory unit 122. The generated data 1200 from the medical device 100 and the virtual private network connection application program 1201 are stored in the non-volatile memory unit 122 of the storage module 12. In an embodiment, the file size of the virtual private network connection application program 1201 is smaller than or equal to one fourth of the storage capacity of the non-volatile memory unit 122. It is noted that the size relationship between the file size of the virtual private network connection application program and the storage capacity of the non-volatile memory unit is not restricted. That is, this size relationship may be varied according to the practical requirements.

In an embodiment, an operation system 1202 is stored in the storage module 12. When the operation system 1202 is executed by the processing control unit 131, the virtual private network connection application program 1201 can be operated under a graphic-based operation interface that is provided by the operation system 1202. In an embodiment, the virtual private network connection application program 1201 contains a virtual private network control code, and the operation system 1202 comprises an operation system control code. The processing control unit 131 executes the virtual private network connection application program 1201 according to the virtual private network control code, and executes the operation system 1202 according to the operation system control code. For example, the operation system 1202 is a Windows operation system, a UNIX operation system, a Mac OS operation system or a Linux operation system. It is noted that the type of the operation system 1202 is not restricted.

In an embodiment, the virtual private network connection application program 1201 contains the server connection setting information. The server connection setting information contains certificate setting information and the client parameter setting information. The certificate setting information includes the root CA certificate, the client certificate or the client key. The client parameter setting information contains the internet protocol address (IP address), the communication protocol setting information (UDP or TCP), the device mode setting information (e.g., a TUN mode or a TAP mode), the user name and password setting information, the encryption method setting information (a Blow Fish encryption method, an AES-128 encryption method, an AES-256 encryption method, a Triple-DES encryption method or a cipher BF-CBC encryption method) and the file compression setting information.

As shown in FIG. 2, the virtual private network connection unit 132 comprises a communication unit 1320. The communication unit 1320 is electrically connected with the processing control unit 131. When the processing control unit 131 executes the virtual private network connection application program 1201 and receives the connection request, the communication unit 1320 is connected to the communication network 300 under control of the processing control unit 131. Consequently, the virtual private network connection unit 132 is connected to the virtual private network server 200 through the communication network 300. For example, the communication unit 1320 is a networking device using a Wi-Fi network, a GSM network or an Ethernet network to implement wireless transmission or wired transmission. It is noted that the type of the communication unit 1320 is not restricted.

The architecture of the memory card device 1 may be implemented with a field programmable gate array (FPGA) or a very large scale integrated circuit (VLSI).

Figure 3:
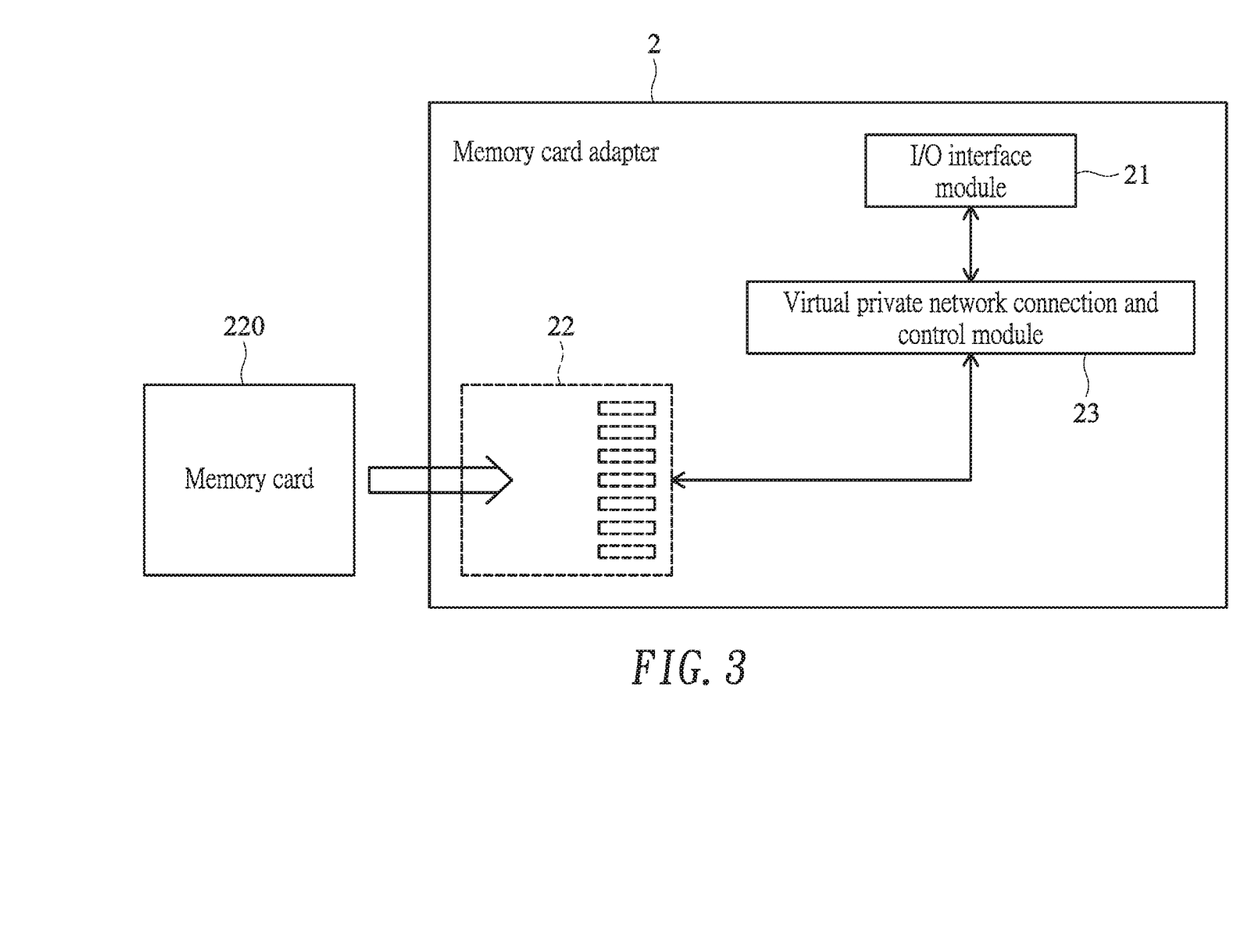
FIG. 3 is a schematic functional block diagram illustrating a memory card adapter according to an embodiment of the present invention.

As mentioned above, the concepts of the present invention may be applied to the memory card device 1 as shown in FIG. 2. In some other embodiments, the concepts of the present invention may be applied to a memory card adapter 2 as shown in FIG. 3. In this situation, the memory card complying with the SD card specification is suitably installed in the medical device, but the memory card complying with the Micro SD card specification cannot be installed in the medical device, When the memory card complying with the Micro SD card specification is installed in the memory card adapter 2 as shown in FIG. 3, the combination of the memory card and the Micro SD card can be considered as the memory card complying with the SD card specification so as to be installed in the medical device.

As shown in FIG. 3, the memory card adapter 2 comprises an I/O interface module 21, an adapting slot 22 and a virtual private network connection and control module 23. The I/O interface module 21 is electrically connected with a medical device. The adapting slot 22 is used for accommodating a memory card 220 (e.g., the Micro SD card). When the memory card 220 is accommodated within the adapting slot 22, the function of the memory card 220 in the memory card adapter 2 is similar to that of the memory storage module 12 in the memory card device as shown in FIG. 2. That is, the data from the medical device and the virtual private network connection application program downloaded by the user are stored in the memory card 220. The virtual private network connection and control module 23 is electrically connected with the I/O interface module 21 and the adapting slot 22. When the virtual private network connection and control module 23 executes the virtual private network connection application program and receives a connection request, the virtual private network connection and control module 23 is connected to a virtual private network server. Consequently, the data stored in the memory card 220 is transmitted to the virtual private network server through the virtual private network connection and control module 23.

The other operations of the memory card adapter 2 are similar to those of the memory card device as shown in FIG. 2, and not redundantly described herein.

From the above descriptions, the present invention provides a virtual private network connection method and a memory card device. A virtual private network connection application program is loaded in a memory card device. The memory card device with the virtual private network connection application program is installed in a medical device. The medical device logins in a virtual private network server through the memory card device with the virtual private network connection application program. Consequently, during the operation of the medical device, the generated data is transmitted to the virtual private network server through the memory card device so as to encrypted and protected. In such way, the data will not be attacked by malware and stolen by a third-party manufacturer during the transmission process.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all modifications and similar structures.

What is claimed is:

1. A virtual private network connection method for obtaining a data generated by a medical device, the method comprising steps of:
   selecting a virtual private network connection application program, which is compatible with a memory card device;
   loading and storing the virtual private network connection application program into the memory card device;
   installing the memory card device, which stores the virtual network connection application program therein, into the medical device;
   making a server connection setting before the virtual private network connection application program is executed;
   executing the virtual private network connection application program stored in the memory card device to a virtual private network in response to a connection request to connect the memory card device to a virtual private network server, which corresponds to the virtual network connection application program; and
   transmitting the data, which is generated from the medical device and stored in the memory card device, to the virtual private network server via the virtual private network;
   wherein the server connection setting includes a certificate setting and a client parameter setting, and wherein a root CA certificate, a client certificate and a client key are generated according to the certificate setting.

2. The virtual private network connection method according to claim 1, wherein the client parameter setting includes a server address setting, a communication protocol setting, a device mode setting, a user name and password setting, an encryption method setting and a file compression setting.

3. The virtual private network connection method according to claim 1, wherein whether the virtual private network connection application program is compatible with the memory card device is determined by judging whether a file size of the virtual private network connection application program is smaller than or equal to a storage capacity threshold value of the memory card device before the virtual private network connection application program is loaded into the memory card device, wherein if the file size of the virtual private network connection application program is smaller than or equal to the storage capacity threshold value of the memory card device, the virtual private network connection application program is loaded into the memory card device.

4. The virtual private network connection method according to claim 3, wherein the storage capacity threshold value is one fourth of a total storage capacity of the memory card device.

5. The virtual private network connection method according to claim 1, wherein the medical device is an ultrasonic scanner, a ventilator, a fundus camera, a continuous positive airway pressure machine or a LED spectrum analyzer.

6. A memory card device installed in a medical device, comprising:
   an I/O interface module electrically connected with the medical device;
   a storage module, wherein a virtual private network connection application program compatible with the storage module is selectively stored in the storage module; and
   a virtual private network connection and control module, which is electrically connected with the I/O interface module and the storage module, communicable with the medical device via the I/O interface module, and communicable with a virtual private network server corresponding to the virtual private network connection application program via a communication network, for receiving and storing a data generated by the medical device into the storage module, making a server connection setting before the virtual private network connection application program is executed, and executing the virtual private network connection application program stored in the storage module to transmit the data stored in the storage module to the virtual private network server;

wherein the server connection setting includes a certificate setting and a client parameter setting, and wherein a root CA certificate, a client certificate and a client key are generated according to the certificate setting.

7. The memory card device according to claim 6, wherein the virtual private network connection and control module comprises:
   a processing control unit electrically connected with the I/O interface module and the storage module for executing the virtual private network connection application program; and
   a virtual private network connection unit electrically connected with and controlled by the processing control unit to transmit data to the virtual private network server.

8. The memory card device according to claim 7, wherein an operation system is further stored in the storage module, and the processing control unit executes at least one of the operation system and the virtual private network connection application program.

9. The memory card device according to claim 7, wherein the data generated from the medical device is received via the I/O interface module and stored into the storage module under the control of the processing control unit.

10. The memory card device according to claim 7, wherein the virtual private network connection unit comprises a communication unit, and the communication unit is electrically connected with the processing control unit, wherein when the processing control unit executes the virtual private network connection application program and receives the connection request, the communication unit is connected to a communication network under control of the processing control unit, so that the virtual private network connection unit is connected to the virtual private network server through the communication network.

11. The memory card device according to claim 10, wherein the communication unit is connected to the communication network in a wireless transmission manner or a wired transmission manner.

12. The memory card device according to claim 6, wherein the storage module comprises a volatile memory unit and a non-volatile memory unit, and the data and the virtual private network connection application program are stored in the non-volatile memory unit.

13. The memory card device according to claim 12, wherein a file size of the virtual private network connection application program is smaller than or equal to one fourth of a total storage capacity of the non-volatile memory unit.

14. The memory card device according to claim 6, wherein the virtual private network connection application program contains a server connection setting information, and the server connection setting information contains a certificate setting information and a client parameter setting information.

15. The memory card device according to claim 14, wherein the certificate setting information includes the root CA certificate, the client certificate and the client key.

16. The memory card device according to claim 14, wherein the client parameter setting information contains an Internet protocol address information, a communication protocol setting information, a device mode setting information, a user name and password setting information, an encryption method setting information and a file compression setting information.

17. The memory card device according to claim 6, wherein the medical device is an ultrasonic scanner, a ventilator, a fundus camera, a continuous positive airway pressure machine or a LED spectrum analyzer.

\* \* \* \* \*